US011338445B2

(12) United States Patent
Bailey et al.

(10) Patent No.: US 11,338,445 B2
(45) Date of Patent: May 24, 2022

(54) END EFFECTOR FORCE SENSOR AND MANUAL ACTUATION ASSISTANCE

(71) Applicant: SYNAPTIVE MEDICAL INC., Toronto (CA)

(72) Inventors: Brent Andrew Bailey, Toronto (CA); Trevor James Dell, Toronto (CA); Bart Verzijlenberg, Toronto (CA); Adam Philip, Toronto (CA); Sean Dowling, Toronto (CA)

(73) Assignee: MACDONALD, DETTWILER AND ASSOCIATES INC., Brampton (CA)

( * ) Notice: Subject to any disclaimer, the term of this patent is extended or adjusted under 35 U.S.C. 154(b) by 214 days.

(21) Appl. No.: 16/115,025

(22) Filed: Aug. 28, 2018

(65) Prior Publication Data

US 2020/0030991 A1    Jan. 30, 2020

(51) Int. Cl.
*A61B 1/00* (2006.01)
*A61B 34/00* (2016.01)
(Continued)

(52) U.S. Cl.
CPC ......... B25J 13/085 (2013.01); *A61B 1/00149* (2013.01); *A61B 34/20* (2016.02);
(Continued)

(58) Field of Classification Search
CPC ...... B25J 13/085; B25J 13/082; B25J 13/084; B25J 9/02; B25J 9/06; B25J 9/1697; B25J 9/1694; B25J 9/16; B25J 19/00; A61B 34/20; A61B 34/32; A61B 34/76; A61B 34/70; A61B 34/74; A61B 34/30;
(Continued)

(56) References Cited

U.S. PATENT DOCUMENTS 9,439,556 B2 *  9/2016  Pandya ................ A61B 1/3132
9,468,501 B2 * 10/2016  Hourtash .............. A61B 34/37
(Continued)

FOREIGN PATENT DOCUMENTS

WO    WO2014152418 A1 *  9/2014  ............ A61B 34/30
WO    WO-2014152418 A1 *  9/2014  ............ A61B 34/76
WO    2018/053361 A1  3/2018

OTHER PUBLICATIONS

"Anand TM, Virtual Sphere Algorithms for Orthodrome-based Collision-free & Smooth Robot Motion, 2009" (Year: 2009).*
(Continued)

*Primary Examiner* — Khoi H Tran
*Assistant Examiner* — Sarah A Tran

(57) ABSTRACT

An automated positioning system and methods of controlling the same. The positioning system includes a multi-joint positioning arm, an end effector coupled to a distal end of the positioning arm, a force-moment sensor (FMS) coupled to the end effector and a controller coupled to communicate with the positioning arm and the FMS. Using signals from the FMS, at least one external force or torque applied to the end effector is determined. A drive velocity for moving the end effector is determined, based on the at least one external force or torque. One or more joint movements of the positioning arm for moving the end effector is calculated, according to the drive velocity. The positioning arm is moved according to the one or more calculated joint movements.

20 Claims, 13 Drawing Sheets

(51) Int. Cl.
*A61B 34/20* (2016.01)
*A61B 34/30* (2016.01)
*A61B 34/32* (2016.01)
*A61B 90/00* (2016.01)
*A61B 90/25* (2016.01)
*B25J 13/08* (2006.01)
*B25J 9/02* (2006.01)
*B25J 9/06* (2006.01)
*B25J 9/16* (2006.01)

(52) U.S. Cl.
CPC .............. *A61B 34/32* (2016.02); *A61B 34/76* (2016.02); *B25J 9/02* (2013.01); *B25J 9/06* (2013.01); *B25J 9/1697* (2013.01); *A61B 2034/2055* (2016.02)

(58) Field of Classification Search
CPC . A61B 34/77; A61B 1/00149; A61B 1/00147; A61B 2034/2055; A61B 2034/2046; A61B 2034/305; A61B 2090/3735; A61B 2090/373; A61B 2090/37; A61B 2090/363; A61B 2090/065; A61B 2090/066; A61B 2090/064; A61B 90/36; A61B 90/25; A61B 90/20; A61B 90/06; G05B 2219/39346; G05B 2219/39; G05B 2219/36432
See application file for complete search history.

(56) References Cited

U.S. PATENT DOCUMENTS

| | | | |
|---|---|---|---|
| 9,668,768 B2* | 6/2017 | Piron | A61B 34/30 |
| 10,779,856 B2* | 9/2020 | Meglan | A61B 34/76 |
| 2015/0081098 A1 | 3/2015 | Kogan | |
| 2015/0100066 A1* | 4/2015 | Kostrzewski | A61B 90/11 606/130 |
| 2015/0127151 A1* | 5/2015 | Riedel | B25J 9/1643 700/250 |
| 2015/0342695 A1* | 12/2015 | He | G01L 1/246 606/130 |
| 2016/0081754 A1 | 3/2016 | Kostrzewski et al. | |
| 2016/0184032 A1 | 6/2016 | Romo et al. | |
| 2016/0202134 A1* | 7/2016 | Malackowski | B25J 13/085 73/862.05 |
| 2016/0296296 A1 | 10/2016 | Bowling et al. | |
| 2017/0086932 A1 | 3/2017 | Auld et al. | |

OTHER PUBLICATIONS

Search report issued by the Intellectual Property Office of the United Kingdom in relation to corresponding GB Application No. GB1813990.7 dated Feb. 13, 2019, 3 pgs.

Examination report issued by the Intellectual Property Office of the United Kingdom in relation to corresponding GB Application No. GB1813990.7 dated Dec. 16, 2021, 2 pgs.

* cited by examiner

END EFFECTOR FORCE SENSOR AND MANUAL ACTUATION ASSISTANCE

CROSS-REFERENCE TO RELATED APPLICATION(S)

This document is a patent application which claims the benefit of, and priority to, Canadian Patent Application No. CA2977380, filed on Aug. 28, 2017, entitled "END EFFECTOR FORCE SENSOR AND MANUAL ACTUATION ASSISTANCE," which is incorporated herein by reference in its entirety.

FIELD

The present disclosure relates to a positioning system for image guided medical procedures. Further, the present disclosure relates to an automated positioning system providing assistance for manual actuation.

BACKGROUND

The present disclosure is generally related to image guided medical procedures using a surgical instrument, such as a fiber optic scope, an optical coherence tomography (OCT) probe, a micro ultrasound transducer, an electronic sensor or stimulator, or an access port based surgery, where a medical navigation system includes a positioning system including a positioning arm, such as a robotic arm, for assisting a surgeon. For example, a robotic arm may automatically position and focus a camera on a surgical site of interest based on tracking information received from the navigation system. Typically, an end effector at the distal end of the positioning arm is used to support a camera, a scope or other medical instrument.

A surgeon may wish to position the camera, scope or other medical instrument held in the end effector in a preferred position and/or orientation. The surgeon may prefer to position the end effector manually, rather than relying solely on the automated positioning that is based on tracking information. In addition, sometimes the positioning arm may run into boundaries, come into contact with another object in the environment or reach the limits of the arm motion, and it may be easier for a user to correct the positioning arm manually. Conventional robotic arms can be awkward at times to manually position. Conventionally, the surgeon may need to press a manual button to release the locks on the robotic arm, which then allows the surgeon to manually move the arm into the desired position. Because of the numerous segments on a typical multi-joint robotic arm, the heavy mass of the robotic arm and/or the mechanical resistance of each joint, it can be difficult and/or tiring to manually move the robotic arm. Further, typically only the segment or joint that is closest to the applied manual force is moved by the manual force. In order to correctly position the entire robotic arm, multiple manual forces may need to be applied at multiple segments or joints of the arm. Again, this can be difficult and/or tiring, and further may create risks for contamination during surgery.

SUMMARY

In various examples disclosed herein, an automated positioning system is described, in which a force-moment sensor (FMS) is used to detect external forces and/or torques applied by a user to an end effector at the distal end of a positioning arm. The positioning arm is controlled such that motors of the positioning arm actively assist the user to move the arm and end effector in response to the applied forces and/or torques. Having the motors of the positioning arm assist the user to move the arm may allow for smoother and/or easier manual actuation of the arm. Such assisted manual actuation may also be referred to as an "intelligent assist" for manual positioning of the arm.

In some aspects, the present disclosure provides an automated positioning system. The positioning system includes a multi-joint positioning arm, an end effector coupled to a distal end of the positioning arm, a force-moment sensor (FMS) coupled to the end effector and a controller coupled to communicate with the positioning arm and the FMS. The controller is configured to: determine, using signals from the FMS, at least one external force or torque applied to the end effector; determine a drive velocity for moving the end effector, based on the at least one external force or torque; calculate one or more joint movements of the positioning arm for moving the end effector according to the drive velocity; and cause the positioning arm to move according to the one or more calculated joint movements.

In some aspects, the present disclosure provides a method for controlling a multi-joint positioning arm. The method includes: determining, using signals from a force-motion sensor (FMS) coupled to the positioning arm, at least one external force or torque applied to an end effector coupled to a distal end of the positioning arm; determine a drive velocity for moving the end effector, based on the at least one external force or torque; calculate one or more joint movements of the positioning arm for moving the end effector according to the drive velocity; and cause the positioning arm to move according to the one or more calculated joint movements.

In some aspects, the present disclosure provides a medical navigation system. The medical navigation system includes the positioning system described above. The medical navigation system also includes at least one of: an imaging system or a medical instrument supported by the end effector. The medical navigation system also includes a plurality of tracking markers coupled to the positioning arm or the end effector of the positioning system, or coupled to the at least one of: the camera, the scope or the medical instrument. The medical navigation system also includes a tracking system for tracking the tracking markers. The controller of the positioning system is configured to: receive tracking information from the navigation system and cause the positioning arm to move with respect to a tracking frame of reference.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
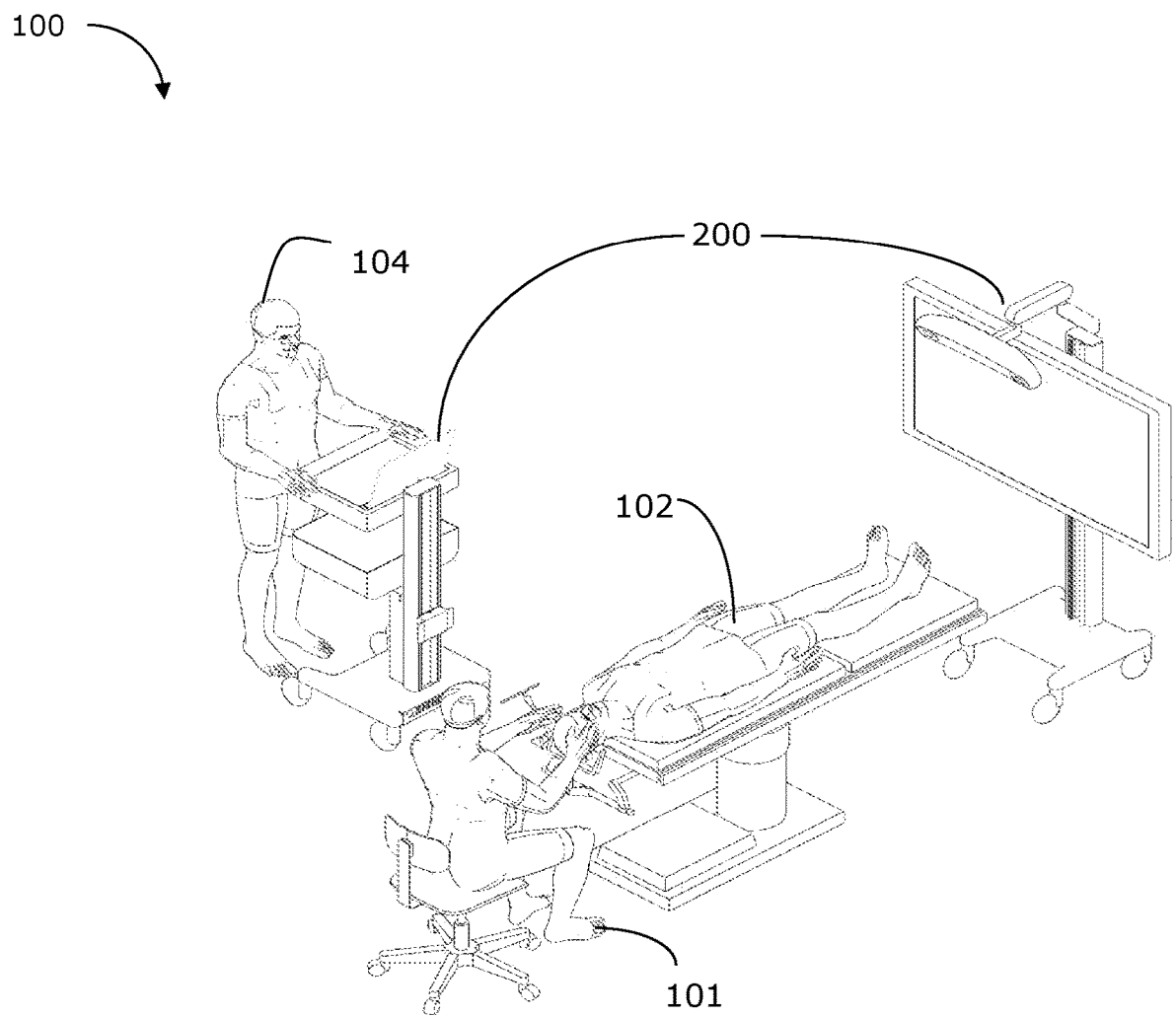
FIG. 1 shows an example operating room setup for an image guided medical procedure.

The systems and methods described herein may be useful for various surgical or non-surgical medical procedures, including spinal procedures, neural procedures, orthopaedic procedures or biopsy procedures. The systems and methods described herein may be useful for controlling a positioning arm in various medical settings. For example, the disclosed methods and systems may be useful for positioning of medical scopes (e.g., microscopes or exoscopes) supported by an end effector at the distal end of the positioning arm. Although described in the context of a neural medical procedure, the teachings of the present disclosure may be applicable to other conditions or fields of medicine, such as other procedures that may benefit from use of a positioning system that provides assistance for manual actuation of the positioning arm.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "preoperative" refers to an action, process, method, event or step that occurs prior to the start of a medical procedure. Preoperative, as defined herein, is not limited to surgical procedures, and may refer to other types of medical procedures, such as diagnostic and therapeutic procedures. Planning a medical procedure may be considered to be preoperative.

Some embodiments of the present disclosure may relate to minimally invasive medical procedures that are performed via an access port or retractor tube, whereby surgery, diagnostic imaging, therapy, or other medical procedures (e.g., minimally invasive medical procedures) are performed based on access to internal tissue through the access port or retractor tube.

In FIG. 1, an operating room (OR) environment 100 is shown, which may be used to support navigated image-guided surgery. As shown in FIG. 1, a surgeon 101 conducts a medical procedure, for example a neurosurgery procedure, on the patient 102 in the OR environment 100. A medical navigation system 200 (described further below) may include an equipment tower, tracking system and display(s) to provide image guidance and/or tracking information, to assist the surgeon 101 during the procedure. An operator 104 may also be present to operate and control the medical navigation system 200, as well as provide other assistance during the medical procedure.

Figure 2:
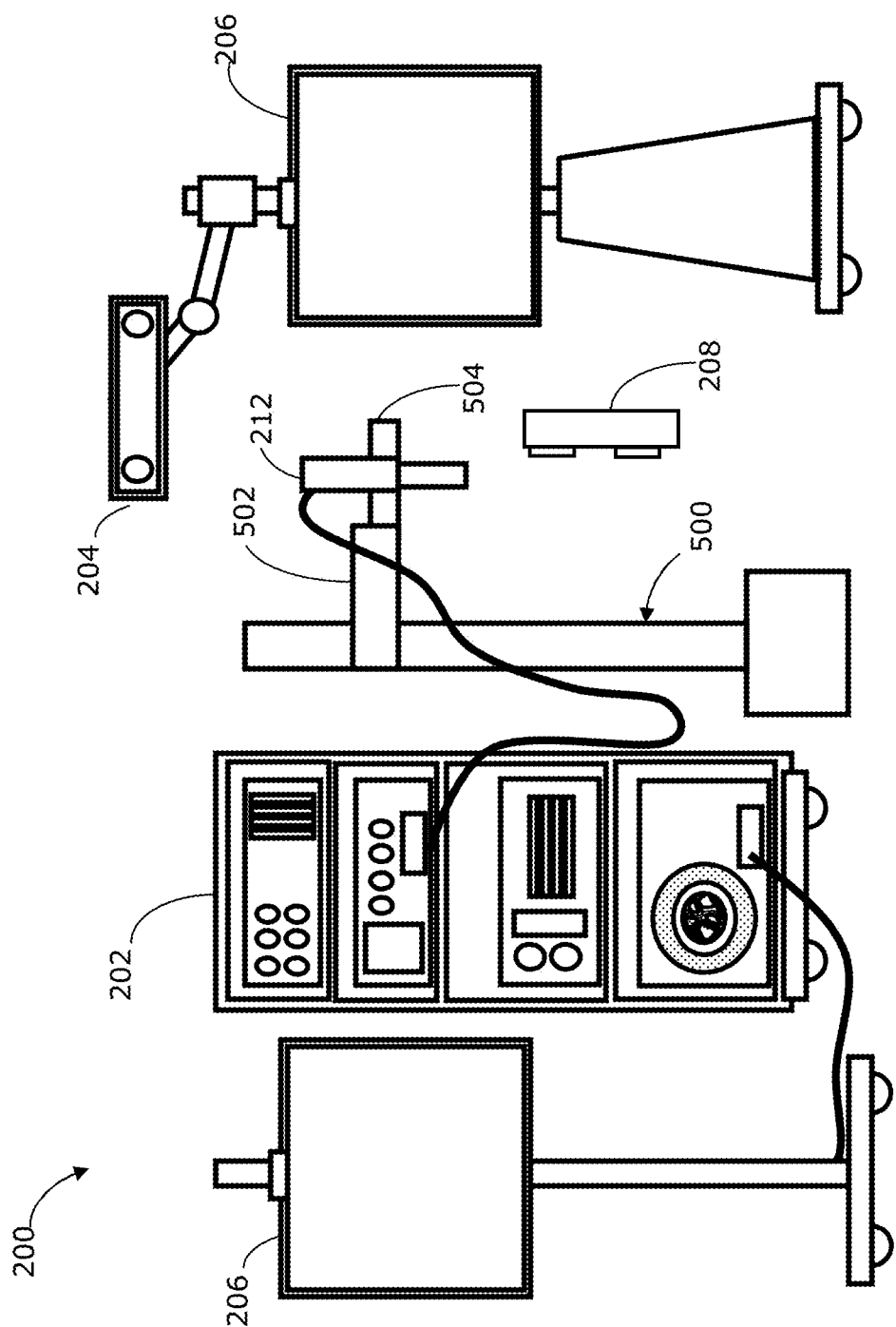
FIG. 2 shows an example navigation system suitable for image guided medical procedures.

FIG. 2 is a diagram illustrating example components of the navigation system 200. The navigation system 200 may provide intraoperative navigation assistance for various medical procedures, including neural procedures, spinal procedures, or other surgical or non-surgical procedures. In the example shown, the navigation system 200 includes an equipment tower 202, a tracking system 204, one or more displays 206, and a positioning system 500. Although described as part of the navigation system 200, in some examples one or more components described with reference to and shown in FIG. 2 may be separate from the navigation system 200 (e.g., the tracking system 204 and/or the positioning system 500 may be a separate system that operates in conjunction with the navigation system 200). The tracking system 204 may include an optical tracking device, tracking camera, video camera, infrared camera, or any other suitable camera or scanner based system. The tracking system 204 may be used to track markers (described further below) to obtain tracking data, which may be used to determine the position and orientation of a tracked object.

The positioning system 500 in this example includes an automated positioning arm 502 (also referred to as a robotic arm or automated arm 502) and an end effector 504 coupled to the distal end of the positioning arm 502. In the example of FIG. 2, the proximal end of the positioning arm 502 is supported by a lifting column. In some examples, the positioning arm 502 may also be supported by a horizontal beam or by any other suitable base. The positioning arm 502 may be a multi-joint positioning arm 502, having multiple segments and joints, for example to enable five, six or seven degrees of freedom. The joints of the multi-joint positioning arm 502 may be independently moved (e.g., by a controller of the positioning system 500) to cause overall movement of the positioning arm, as discussed further below.

The end effector 504 may support one or more instruments and/or tools for the medical procedure. In FIG. 2, the end effector 504 is shown as holding an intraoperative imaging system 212 such as a medical digital microscope, however it should be noted that any alternate devices may be used with the end effector 504 including a wide field camera, microscope and Optical Coherence Tomography (OCT), video camera, or other imaging instruments, as well as non-imaging devices. In some examples, the intraoperative imaging system 212 may include a wide field camera in connection with an external scope, which may be held together by a single end effector 504. In another example, multiple end effectors 504 may be coupled to the positioning arm 502, for example to hold different imaging systems to enable switching among multiple imaging modalities. In some examples, different end effectors 504 may provide different ranges of control (e.g., a micro-control effector may be used to hold a tool requiring finer control, such as a laser-based ablation system). Use of multiple end effectors 504 may require particular placement of the end effectors 504 on the positioning arm 502, to avoid mutual interference, for example. The placement of the end effectors 504 may also be important to enable accurate detection of forces and torques applied to an end effector 504, as described further below.

The positioning system 500 may receive input information about the spatial position and orientation of the positioning arm 502, end effector 504 and/or tool held by the end effector 504 (e.g., the imaging system 212), for example from the tracking system 204. The position and orientation of the positioning arm 502, end effector 504 and/or held tool may be determined by the tracking system 204 by detection of markers provided on the positioning arm 502, end effector 504 and/or held tool. In some examples, position sensors (not shown) on the positioning arm 502 may provide information about the position and orientation of the positioning arm 502 (e.g., the position and orientation of each segment and/or joint of a multi-joint positioning arm 502), and the position and orientation of the end effector 504 and/or held tool may be determined based on the known position and orientation of the end effector 504 and/or held tool relative to the positioning arm 502. The positioning system 500 may also receive information from the tracking system 204 about the position and orientation of any other tracked object.

The positioning system 500 may work in conjunction with the tracking system 204 to position the intraoperative imaging system 212 to maintain alignment with an object of interest, such as aligned with the passage of an access port.

For example, the positioning system 500 may compute the desired joint positions for the positioning arm 502 so as to manoeuvre the end effector 504 to a predetermined spatial position and orientation relative to the tracked object. This predetermined relative spatial position and orientation may be designated as the "Zero Position", such as where the field-of-view (FOV) of the imaging system 212 is aligned with the tracked object.

Further, the positioning system 500, the tracking system 204 and the positioning arm 502 may form a feedback loop. This feedback loop may work to keep the tracked object in constant view and focus of the imaging system 212 (e.g., where the end effector 504 holds the imaging system 212), as the tracked object may move during the procedure. The positioning system 500 may also include an input mechanism, such as a foot pedal, which may be activated to control the positioning arm 502 to automatically align the imaging system 212 (e.g., held by the end effector 504) with the tracked object. The positioning system 500 may also provide an intelligent assist for manual actuation of the positioning arm 502, as discussed further below.

A handheld three-dimensional (3D) scanner 208 may be used to capture intraoperative 3D image data about an object of interest, such as the surface of the surgical site. The 3D scanner 208 may be used to capture a full or nearly full array scan of a patient's surface (e.g., a patient's face in the case of a neural procedure). This 3D image data may be provided as a 3D point cloud and may be used for registration purposes (e.g., mapped to preoperative and/or intraoperative images).

Image data (e.g., intraoperative image data captured by the imaging system 212) may be displayed on one or more of the display(s) 206. The display(s) 206 may display intraoperative image data, preoperative image data, such as preoperative image data (e.g., MR or CT image data) or 3D image data, as well as other navigation information. The displayed image data may be co-registered and displayed overlaid with each other, for example.

Figure 3:
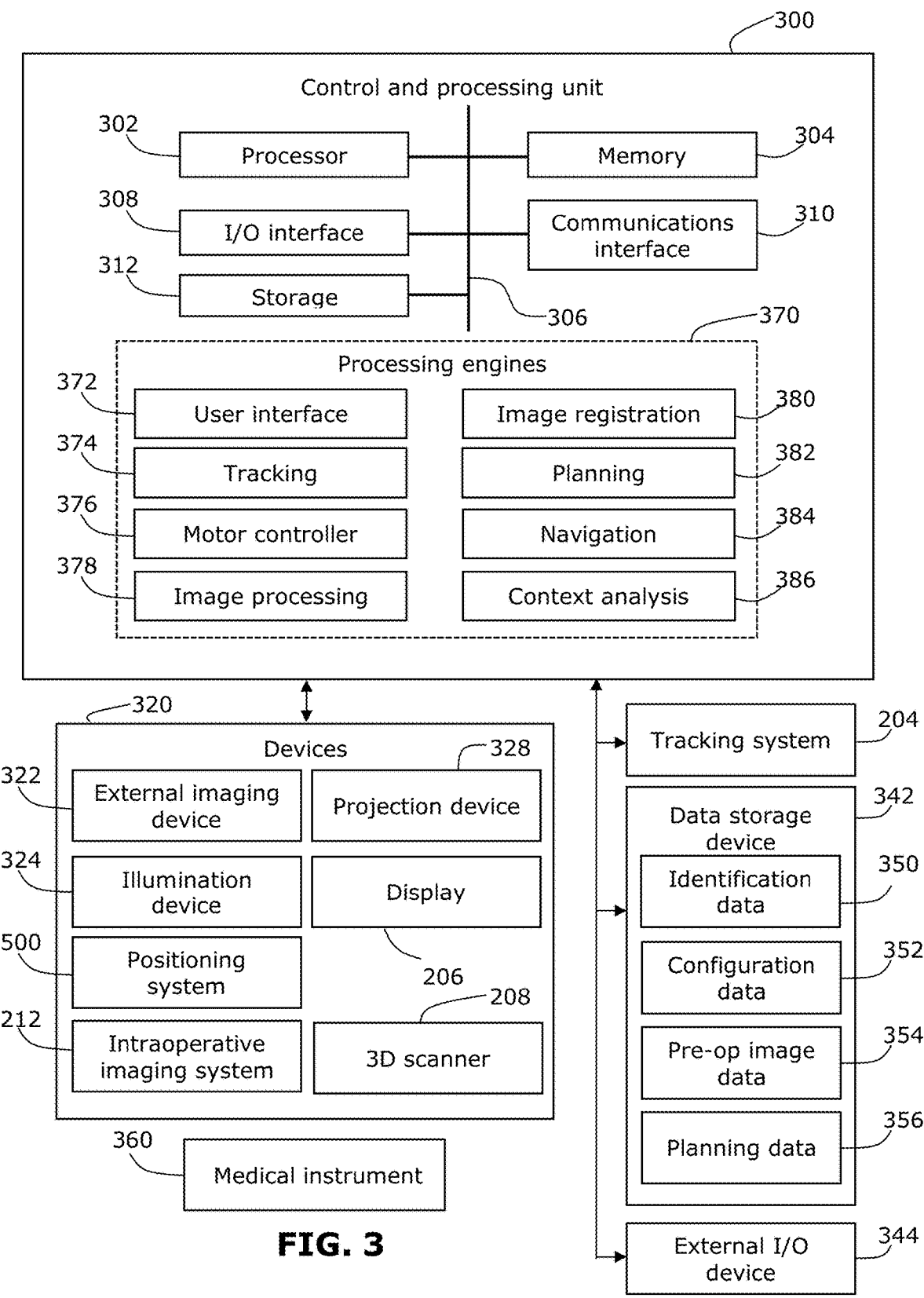
FIG. 3 is a block diagram illustrating an example control and processing system that may be used in the navigation system of FIG. 2.

In FIG. 3, a block diagram is shown illustrating a control and processing unit 300 that may be used in the medical navigation system 200 (e.g., as part of the equipment tower 202). Although FIG. 3 shows and is described with reference to a single instance of each component, in some examples there may be multiple instances of certain components.

As shown in FIG. 3, in an example, the control and processing system 300 may include a processor 302, a memory 304, a system bus 306, an input/output interface 308, a communications interface 310, and a storage device 312. The control and processing system 300 may be interfaced with other external devices/systems, such as the tracking system 204, a data storage device 342, and an external input and output device 344, which may include, for example, one or more of a display, keyboard, mouse, sensors attached to medical equipment, foot pedal, microphone or speaker. The data storage device 342 may be any suitable data storage device, such as a local or remote computing device (e.g. a computer, hard drive, digital media device, or server) having a database stored thereon.

In the example shown in FIG. 3, the data storage device 342 includes identification data 350 for identifying one or more medical instruments 360 and configuration data 352 that may associate configuration parameters with one or more of the medical instrument(s) 360. The data storage device 342 may also include preoperative image data 354 and/or medical procedure planning data 356. Although the data storage device 342 is shown as a single device in FIG.

3, in some examples the data storage device 342 may be provided as multiple storage devices.

The medical instrument 360 may be identifiable by the control and processing unit 300. The medical instrument 360 may be connected to and controlled by the control and processing unit 300, or the medical instrument 360 may be operated or otherwise employed independent of the control and processing unit 300. The tracking system 204 may be employed to track one or more of the medical instrument(s) 360. For example, one or more tracking markers may be provided on the medical instrument 360, or the medical instrument 360 may be coupled to a tracked object (e.g., a trackable sheath or a trackable frame).

The control and processing unit 300 may also interface with one or more devices 320, which may include configurable devices. The control and processing unit 300 may intraoperatively reconfigure one or more of such devices 320 based on configuration parameters obtained from the configuration data 352. Example devices 320 include an external imaging device 322, an illumination device 324, the positioning system 500, the intraoperative imaging system 212, a projection device 328, the display 206, and the 3D scanner 208.

The control and processing unit 300 may implement examples described herein, via the processor 302 and/or memory 304. For example, the functionalities described herein can be implemented via hardware logic in the processor 302 and/or using instructions stored in the memory 304, as one or more processing modules or engines 370. Example processing engines 370 include, but are not limited to, a user interface engine 372, a tracking engine 374, a motor controller 376, an image processing engine 378, an image registration engine 380, a procedure planning engine 382, a navigation engine 384, and a context analysis engine 386. While the example processing engines 370 are shown separately in FIG. 3, in some examples the processing engines 370 may be collectively stored as one or more sets of computer-readable instructions (e.g., stored in the memory 304). In some examples, two or more processing engines 370 may be used together to perform a function.

It is to be understood that the system is not intended to be limited to the components shown in FIG. 3. One or more components of the control and processing system 300 may be provided as an external component or device. For example, the navigation module 384 may be provided by an external navigation system that is integrated with the control and processing system 300

In some examples, the navigation system 200, which may include the control and processing unit 300, may provide tools to the surgeon that may help to improve the performance of the medical procedure and/or post-operative outcomes. In addition to neural procedures, the navigation system 200 can also be used in the context of an orthopaedic procedure or a spinal procedure, as well as medical procedures on other parts of the body such as breast biopsies, liver biopsies, and others. While some examples are described herein, examples of the present disclosure may be applied to any suitable medical procedure.

Generally, the intraoperative image data obtained by the intraoperative imaging device 212 is in a coordinate space different from and independent of the coordinate space of the preoperative image data (e.g., MR or CT image data). More generally, different sets of image data may be in different coordinate spaces, even where the image data are all obtained intraoperatively or all obtained preoperatively, and even where the image data are obtained using the same imaging modality. As well, tracking data obtained by the tracking system 204 is in a coordinate space different from and independent of the image coordinate spaces. Data obtained by the 3D scanner 208 generally are also in a different coordinate space.

Co-registration of these different sets of data may be achieved by performing a transformation mapping to map the sets of data into a common coordinate space. This mapping may also be referred to as co-registration of the sets of data, so that two or more of these data sets can be presented together (e.g., using visual overlays) to provide navigation assistance to the surgeon during the medical procedure.

Figure 4:
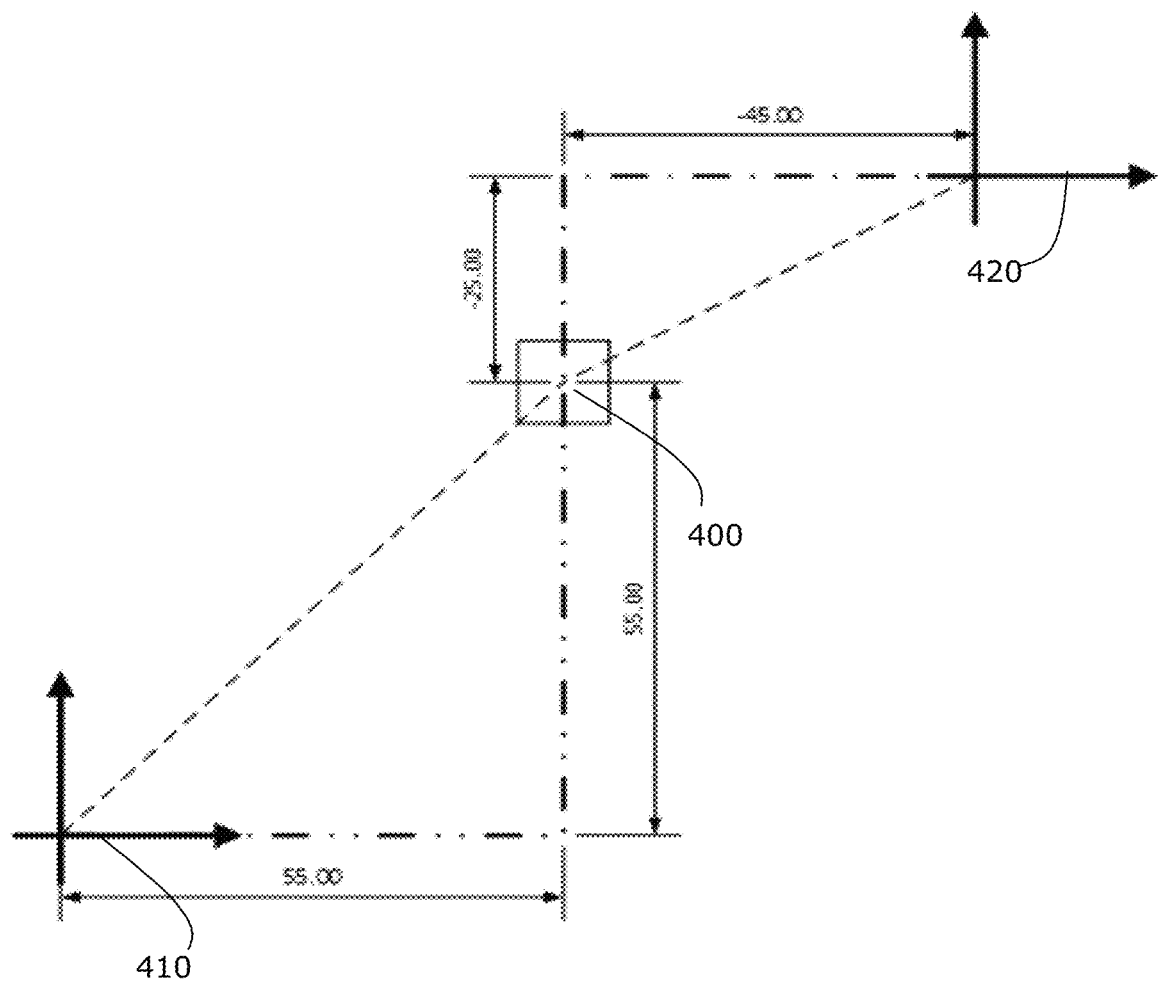
FIG. 4 is a diagram illustrating co-registration of two coordinate spaces.

FIG. 4 illustrates a simplified example of how two coordinate spaces may be co-registered by performing a transformation mapping, based on a common reference coordinate. For simplicity, although FIG. 4 illustrates co-registration of 2D coordinate spaces, co-registration may be performed for 3D coordinate spaces, including a depth dimension.

In the example shown, a common reference coordinate 400 has a defined position and orientation in first and second coordinate spaces 410, 420. In the context of a medical procedure, the common reference coordinate 400 may be a fiducial marker or anatomical reference. In some examples, the common reference coordinate 400 may be provided by a patient reference device, described further below. Co-registration of different pairs of coordinate spaces may be performed using different common reference coordinates, to arrive at a common coordinate space for all data sets.

For simplicity, co-registration of two coordinate spaces is now described with reference to FIG. 4. The position and orientation of the common reference coordinate 400 is used to correlate the position of any point in the first coordinate space 410 to the second coordinate space 420, and vice versa. The correlation is determined by equating the locations of the common reference coordinate 400 in both spaces 410, 420 and solving for a transformation variable for each degree of freedom defined in the two coordinate spaces 410, 420. These transformation variables may then be used to transform a coordinate element of a position in the first coordinate space 410 to an equivalent coordinate element of a position in the second coordinate space 420, and vice versa.

In FIG. 4, the common reference coordinate 400 has a coordinate position (x1, y1) determined in the first coordinate space 410 and a coordinate position (x2, y2) in the second coordinate space 420. In the example shown, (x1, y1)=(55, 55) and (x2, y2)=(−45, −25).

Utilizing transformation equations, any point in the first coordinate space 410 may be related to the second coordinate space 420 via translation variables (xT, yT), as shown below:

$$x1=x2+xT$$

$$y1=y2+yT$$

Using the coordinate positions of the common reference coordinate 400, the transformation variables may be solved as follows:

$$55=-45+yT$$

$$100=yT$$

$$55=-25+xT$$

$$80=xT$$

The transformation variables may then be used to transform any coordinate point in the first coordinate space 410 to the second coordinate space 420, and vice versa, thereby co-registering the coordinate spaces 410, 420. For transformation between 3D coordinate spaces, similar calculations may be performed for position (x, y, z-coordinates) as well as for orientation (pitch, yaw, roll). In general, a transformation mapping may be performed to register two or more coordinate spaces with each other. Where there are more than two coordinate spaces to be co-registered, the transformation mapping may include multiple mapping steps.

Figure 5:
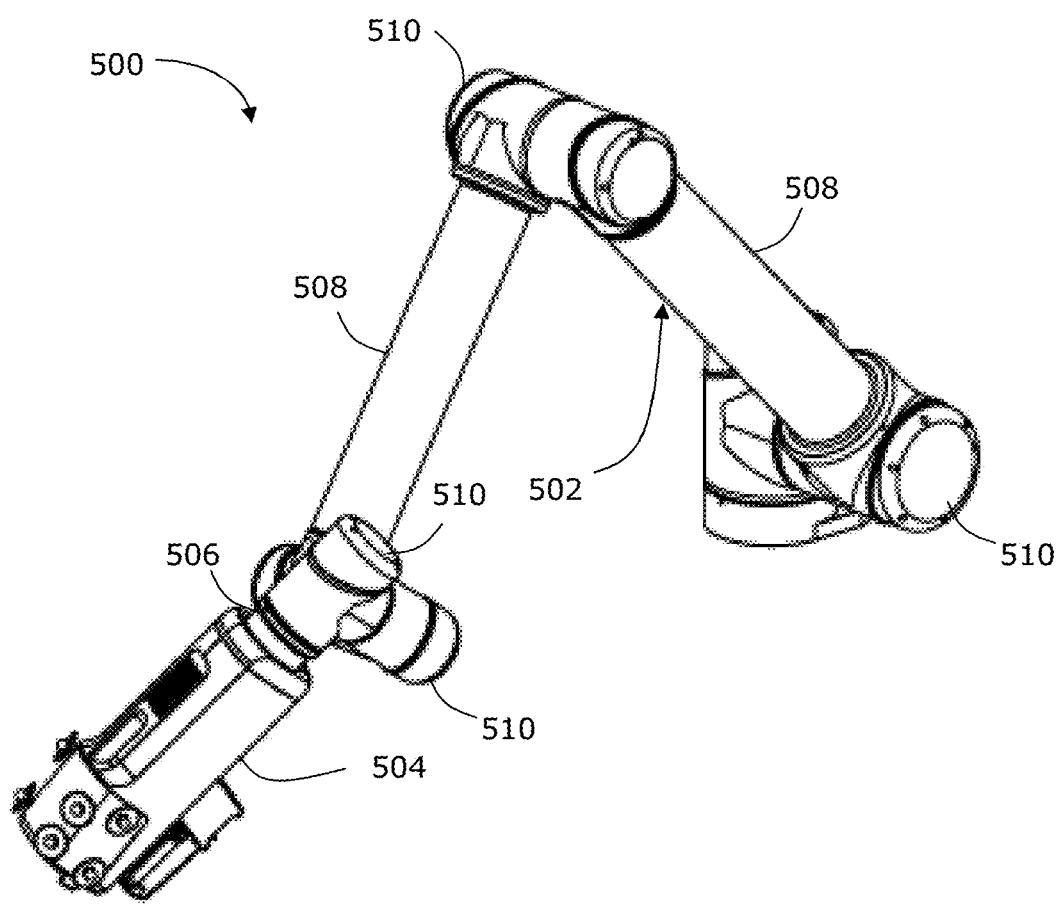
FIG. 5 is a perspective view of an example automated positioning arm with an end effector coupled at the distal end.
Figure 6:
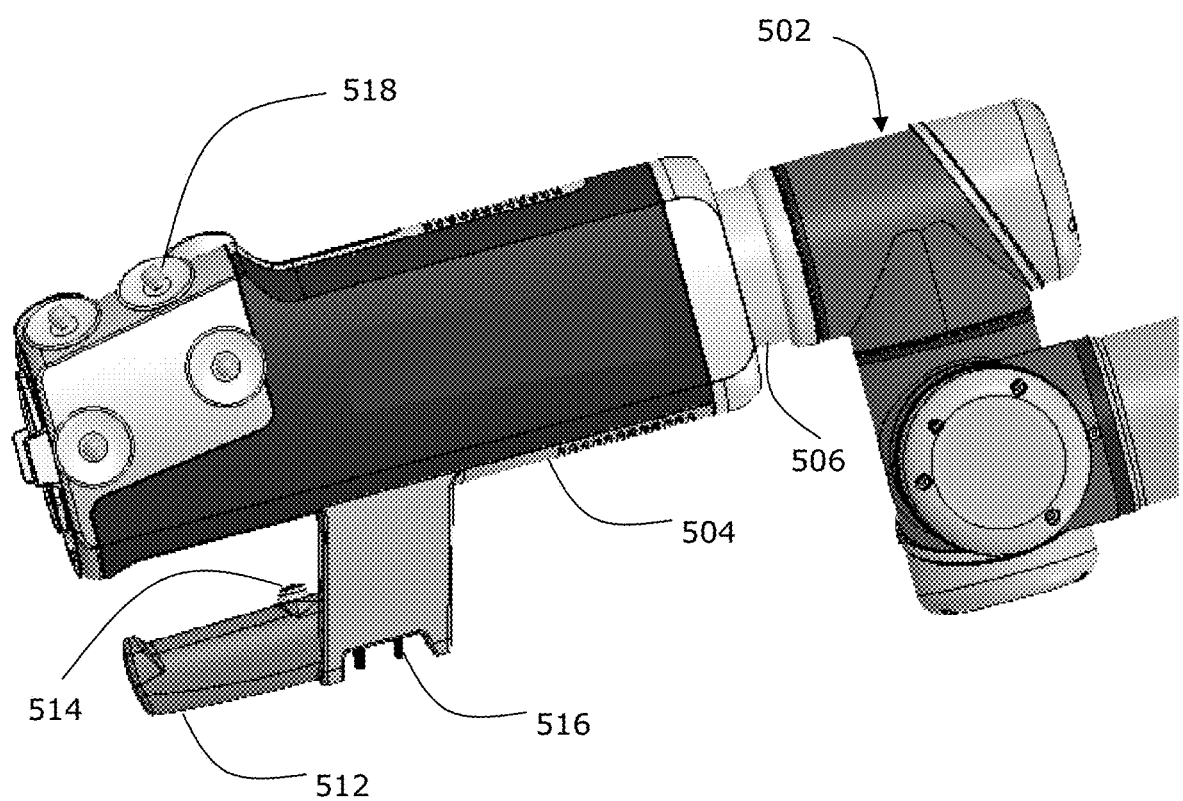
FIG. 6 is a close up view of the end effector and distal end of the positioning arm of FIG. 5.

FIG. 5 illustrates an example positioning system 500 including a multi-joint positioning arm 502 and an end effector 504 coupled to the distal end of the positioning arm 502. FIG. 6 provides a closer view of the end effector 504 and the distal end of the positioning arm 502. FIGS. 5 and 6 will be discussed together. A controller (not shown) communicates with and controls movement of the positioning arm 502. The multi-joint positioning arm 502 includes a number of arm segments 508 connected by joints 510. In one example, the function of the controller may be performed by a computing device such as the control and processing unit 300 of FIG. 3. Some or all control functions for controlling the positioning system 500 may be performed by the controller of the navigation system 200. In some examples, the positioning system 500 may be partly or fully controlled by a controller separate from the navigation system 200 (e.g., where the positioning system 500 is a separate system from the navigation system 200).

A force-moment sensor (FMS) 506 is coupled to the end effector 504. In the example shown, the FMS 506 is coupled between the distal end of the positioning arm 502 and the end effector 504. The FMS 506 may be coupled to the end effector 504 in any suitable position for detecting forces and torques applied to the end effector 504. For example, the FMS 506 may be coupled to the end effector 504 at any location between the distal end of the positioning arm 502 and the location where external forces/torques are applied (e.g., a handle, described further below). The FMS 506 may be integrated with the end effector 504 in some examples.

In examples where there are multiple end effectors 504, each end effector 504 may be coupled with a respective FMS 506, and the force/torque signals from each FMS 506 may be distinguishable from each other, in order to distinguish the forces/torques applied to each respective end effector 504. In some examples, only a subset of the multiple end effectors 504 may be provided with a FMS 506. In other examples, one FMS 506 may be used to sense forces/torques at multiple end effectors 504, in which case the specific end effector 504 to which external forces/torques are manually applied is identified by input signals (e.g., user selection of a particular end effector 504 or user activation of a button on the particular end effector 504). In order for a single FMS 506 to accurately sense forces/torques at multiple end effectors 504, the FMS 506 may be coupled between the distal end of the positioning arm 502 and the multiple end effectors 504. In the examples described above, the different end effectors 504 may be coupled to the positioning arm 502 at the same time, or may be switched with each other as appropriate. If multiple end effectors 504 are coupled to the positioning arm 502 at the same time, only one end effector 504 may be active at any given time and the FMS 506 may be configured to sense forces/torques at the one active end effector 504. In some examples, two or more end effectors 504 may be active at any given time, and one or more FMSs 506 may be used to appropriately sense forces/torques at the active end effectors 504.

The end effector 504 may include a handle 512 to facilitate manual actuation of the positioning arm 502. In some examples, the FMS 506 may be coupled to the handle 512, so as to more directly detect forces and torques applied by a user to the end effector 504 via the handle 512. A manual activation mechanism, such as a button 514, may be provided on the end effector 504, for example on a trigger position on the handle 512. Depression of the button 514 (e.g., by a finger of a hand gripping the handle 512) may be required to enable manual actuation of the positioning arm 502. This may be a safety feature, to avoid inadvertent actuation of the positioning arm 502. One or more other activation mechanisms, such as switch(es) 516 may be provided on the end effector 504, for example on a thumb-accessible position on the handle 512. The switch(es) 516 may be used to control other functions of the positioning system 500, for example to select a control mode (discussed further below). In the present disclosure, manual activation/actuation may include any activation/actuation performed physically by the user, and includes activation/actuation by a hand, a foot or any other part of the user's body. Thus, a manual activation mechanism may include a foot pedal in some examples.

As previously noted, the positioning system 500 may be tracked by the tracking system 204 of the navigation system 200. For example, a plurality of tracking markers 518 may be coupled to the positioning arm 502 and/or the end effector 504. In the example shown, a plurality of tracking markers 518 (e.g., reflective spheres) are coupled near the distal end of the end effector 504. The tracking markers 518 may be positioned such that, as the end effector 504 changes position and orientation, a sufficient number of tracking markers 518 remain detectable by the tracking system 204 to accurately track the position and orientation of the end effector 504.

The position and orientation of the end effector 504 and the positioning arm 502 (e.g., as defined by individual segments 508 and joints 510) may also be determined by sensors integrated into the positioning arm 502 that track movement of the individual segments 508 and joints 510. Other sensors may be mounted to the positioning system 500 as appropriate.

The end effector 504 may support any suitable tool, such as a camera, a scope, a laser, a spectrometer, a drill or any suitable medical instrument. In some examples, a tool, such as camera (e.g., 2D optical camera) or a scope (e.g., a medical digital microscope) may be integrated into the end effector 504. By integrating the tool into the end effector 504, the total weight of the end effector 504 may be known and fixed, without having to account for variable weight of external devices that may be attached to the end effector 504. In the example shown, an imaging system, such as a scope, is supported by and integrated with the end effector 504. The optical axis of the scope may be aligned with the main longitudinal axis of the end effector 504, to facilitate intuitive control.

Although a particular end effector 504 is shown, the end effector 504 may be interchangeable. For example, the coupling between the end effector 504 and the distal end of the positioning arm 502 may be releasable to enable a different end effector or other tool to be coupled to the distal end of the positioning arm 502.

Figure 7:
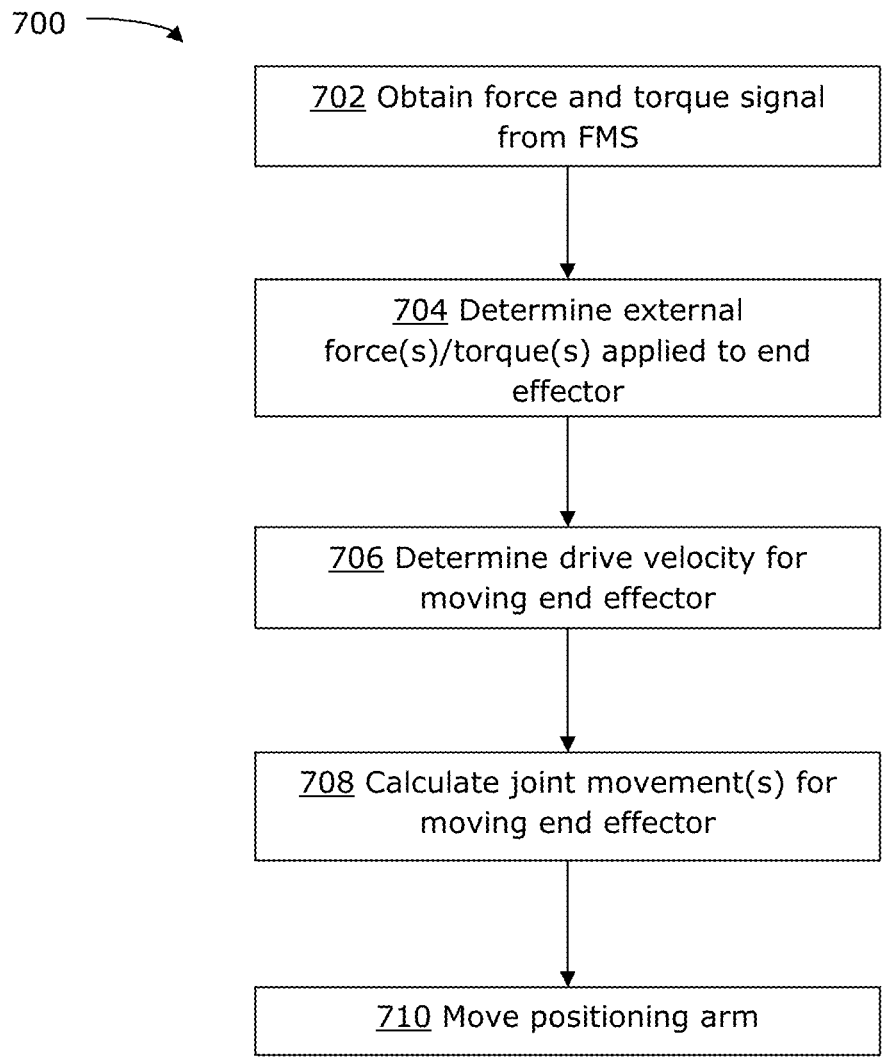
FIG. 7 is a flowchart illustrating an example method for controlling the positioning arm in response to external forces and/or torques.

FIG. 7 is a flowchart illustrating an example method 700 for controlling the positioning system 500. The method 700 may be performed by a controller of the positioning system 500 and/or a controller external to the positioning system 500. The controller is coupled to communicate with the positioning arm 502 and the FMS 506 of the positioning system 500. In some examples, the controller may also be coupled to communicate with the end effector 504 and/or an imaging system or other tool supported by the end effector 504.

The method 700 may be initiated in response to input from the user. For example, the user may activate a manual activation mechanism, such as the button 514, to initiate manual actuation of the positioning arm 502. The requirement to activate an activation mechanism may be a safety feature to avoid unintentional movement of the positioning arm 502 (e.g., due to accidentally bumping into the arm 502).

At 702, force and torque signal(s) is(are) obtained from the FMS 506. The force and torque signal(s) may be provided by the FMS 506 in response to a request from the controller or may be regularly provided by the FMS 506, for example.

At 704, the controller determines one or more external forces and/or torques applied to the end effector 504, based on the force and torque signal(s). Determining the external force(s) and/or torque(s) may involve subtracting known internal forces and torques from the force(s) and torque(s) detected by the FMS 506. Internal forces and torques refer to the forces and torques experienced by the end effector 504 due to the end effector's own mass, and include forces and torques due to gravity. The internal forces and torques may be calculated based on properties of the end effector 504 that are known beforehand. For example, the total mass and center of mass of the end effector 504 (including any unsupported cables) and the tool held by the end effector 504 may be known beforehand (e.g., through design and/or testing). This may be the case particularly where the tool is integrated into the end effector 504. The internal forces and torques may be calculated for the end effector 504 at the time prior to activation of the manual activation mechanism, for example.

At 706, the controller determines a drive velocity for moving the end effector 504, based on the external force(s)/torque(s). The drive velocity may include more than one component, for example including the desired linear and angular velocity (both referred generally to as drive velocity for short) at which the end effector 504 should be moved. The relationship between the drive velocity and the applied external force(s)/torque(s) may be linear or non-linear (e.g., according to different control modes described further below). A damping effect may be implemented to ensure smooth motion of the end effector 504.

In examples where the FMS 506 is not located at the location where the external force(s)/torque(s) is(are) applied by the user (e.g., the FMS 506 is not located at the handle 512 of the end effector 504), a transformation may be applied to transform the external force(s)/torque(s) from the FMS frame of reference to the end effector frame of reference, where the end effector frame of reference is defined relative to the location where external force(s)/torque(s) are expected to be applied. By providing the handle 512 on the end effector 504 and requiring activation of a button 514 on the handle 512, this configuration may help to ensure that the user applies external force(s)/torque(s) at the expected location.

The transformation from the FMS frame of reference to the end effector frame of reference may be determined beforehand, for example through design and testing, or at a calibration step prior to the method 700.

The transformation may be calculated based on the known fixed relationship between the FMS 506 and the end effector 504, or by relating the FMS 506 and the end effector 504 to a common reference coordinate, for example. In some examples, the transformation may be from the FMS frame of reference to any frame of reference (e.g., a common frame of reference) that can be used by the controller to calculate drive velocity.

The drive velocity may be determined according to one of a plurality of available control modes. The user may select a desired control mode using a suitable interface, such as the switch(es) 516 provided on the end effector 504. In the absence of user selection, a default control mode (e.g., free mode) may be automatically used. The selectable control modes may include, for example, translation mode, roll mode, stand-off mode, orbit mode, memory mode or free mode. FIGS. 8-12 illustrate control of the positioning system 500 according to example control modes. In some examples, two or more of the control modes may be used in combination (e.g., orbit mode may be used with roll mode or stand-off mode). Other control modes may be possible, including other control modes that include aspects of the control modes illustrated in FIGS. 8-12.

Figure 8A:
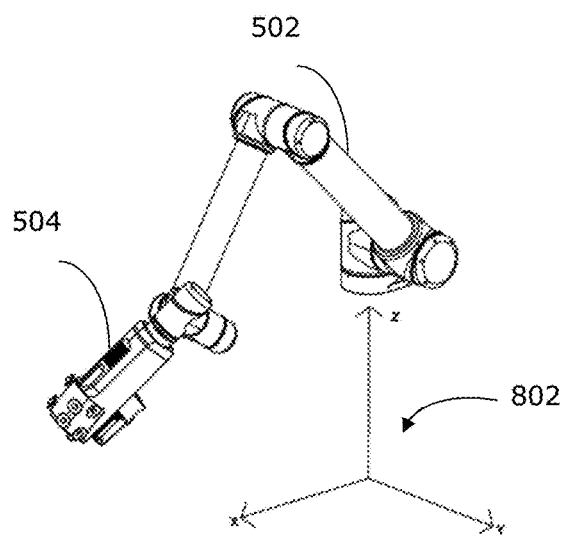
FIGS. 8A-8D illustrate the movement of the end effector when the positioning system is controlled in translation mode from an original position (FIG. 8A), to movement in z-direction (FIG. 8B), to movement in x-direction (FIG. 8C), and to movement in y-direction (FIG. 8D).
Figure 8B:
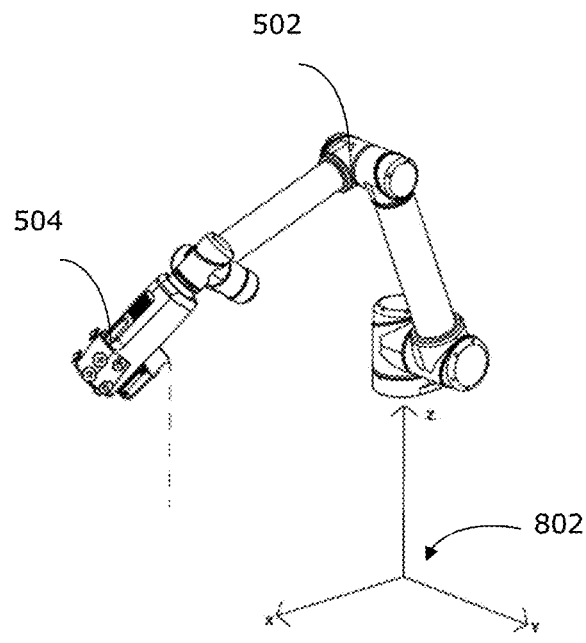
Figure 8C:
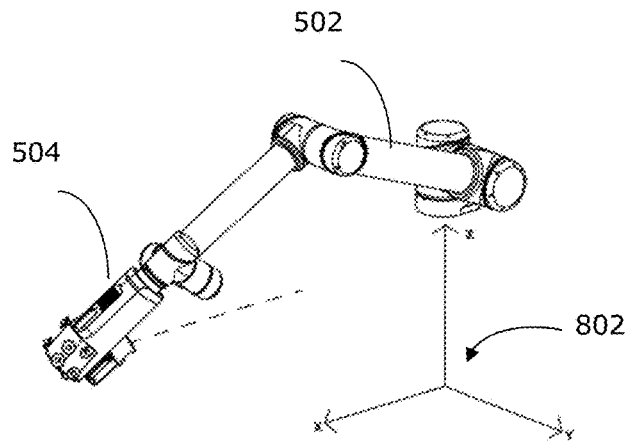
Figure 8D:
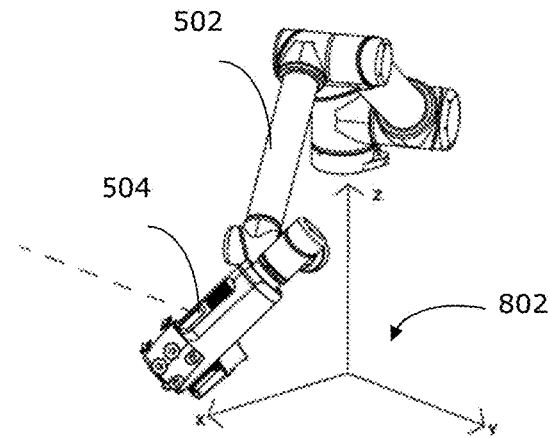

FIGS. 8A-8D illustrate the movement of the end effector 504 when the positioning system 500 is controlled in translation mode from an original position (FIG. 8A), to movement in z-direction (FIG. 8B), to movement in x-direction (FIG. 8C), and to movement in y-direction (FIG. 8D). In translation mode, only external forces are used to determine the drive velocity, and the drive velocity may include only linear velocity components. Any external torques are ignored or set to zero. Translation mode may be useful in the scenario where the end effector 504 supports an imaging system capturing an image of the medical procedure (e.g., resection of a tumor). When the surgeon needs to view portions of the surgical site outside of the captured image (e.g., the tumor has been removed up to the edge of the captured image), translation mode may be used to move the end effector 504 (and the supported imaging system) while keeping the same relative view. FIG. 8A shows the positioning arm 502 and end effector 504 with respect to a Cartesian coordinate 802, which may be defined with respect to the frame of reference of the positioning system 500 or other frame of reference. The drive velocity for the end effector 504 includes only linear components, for example movement in the z-direction (FIG. 8B), x-direction (FIG. 8C), y-direction (FIG. 8D) or combinations thereof. The orientation of the end effector 504 is kept constant during these translation movements.

Figure 9A:
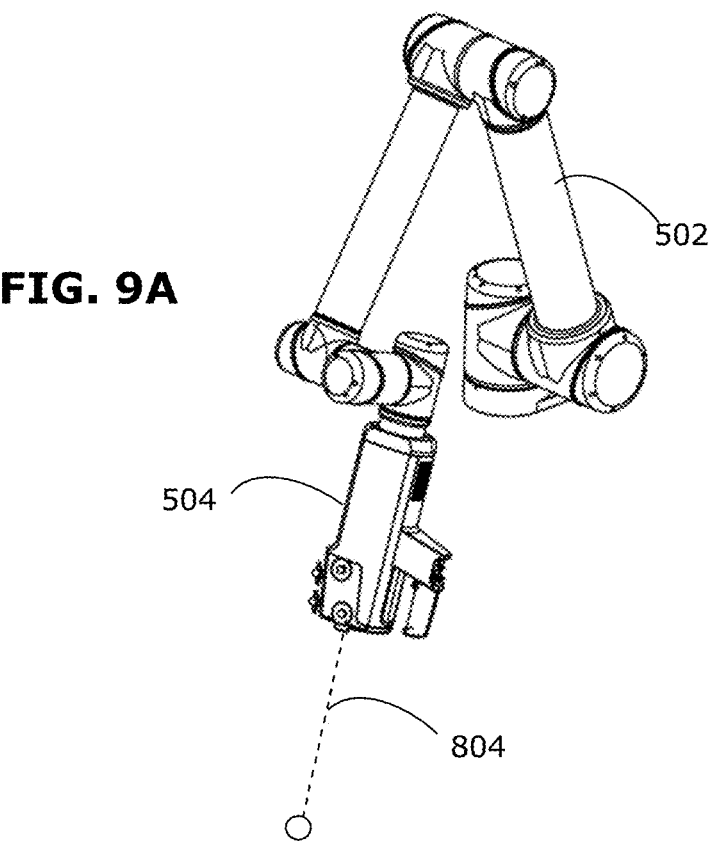
FIGS. 9A and 9B illustrates the movement of the end effector when the positioning system is controlled in roll mode from a first position of the end effector (FIG. 9A) to a second position of the end effector (FIG. 9B)
Figure 9B:
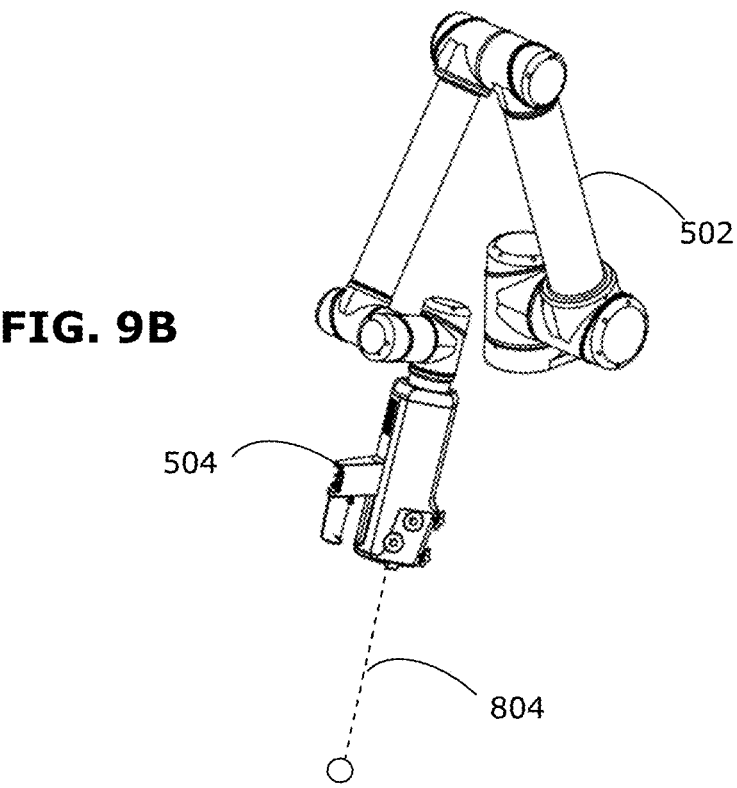

FIGS. 9A and 9B illustrates the movement of the end effector 504 when the positioning system 500 is controlled in roll mode from a first position of the end effector (FIG. 9A) to a second position of the end effector (FIG. 9B) In roll mode, only external torques are used to determine the drive velocity, and the drive velocity may include only angular velocity components. Any external forces are ignored or set to zero. Further, roll mode may consider only external torques applied about a defined axis, such as the main axis of the end effector 504 or the optical axis of a scope supported by the end effector 504, and ignore or zero all other torques. Roll mode may be used if the surgeon wishes to change the orientation of an image captured by an imaging system supported by the end effector 504, for example to match the orientation of the image with the orientation of the surgeon with respect to the surgical site, without changing the focus or field-of-view of the captured image. FIGS. 9A and 9B show the end effector 504 rotating about a defined axis 804, for example the optical axis of an imaging system supported by the end effector 504. The focal point of the imaging system is represented by a circle at the end of the defined axis 804. Although the orientation of the end effector 504 changes, the position of the end effector 504 is kept constant.

Figure 10A:
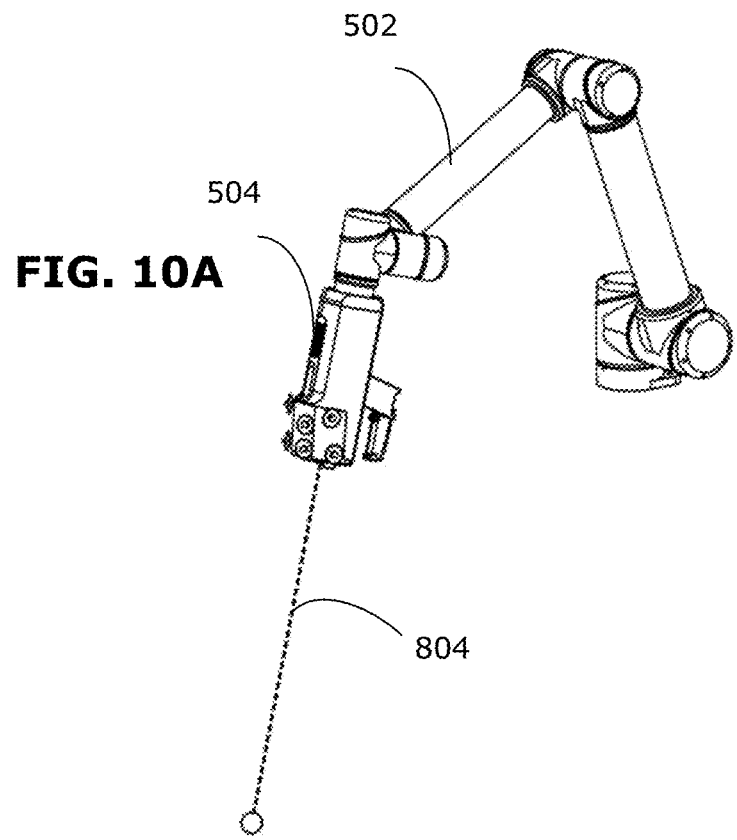
FIGS. 10A and 10B illustrate the movement of the end effector when the positioning system is controlled in stand-off mode from a first position of the end effector (FIG. 10A) to a second position of the end effector (FIG. 10B).
Figure 10B:
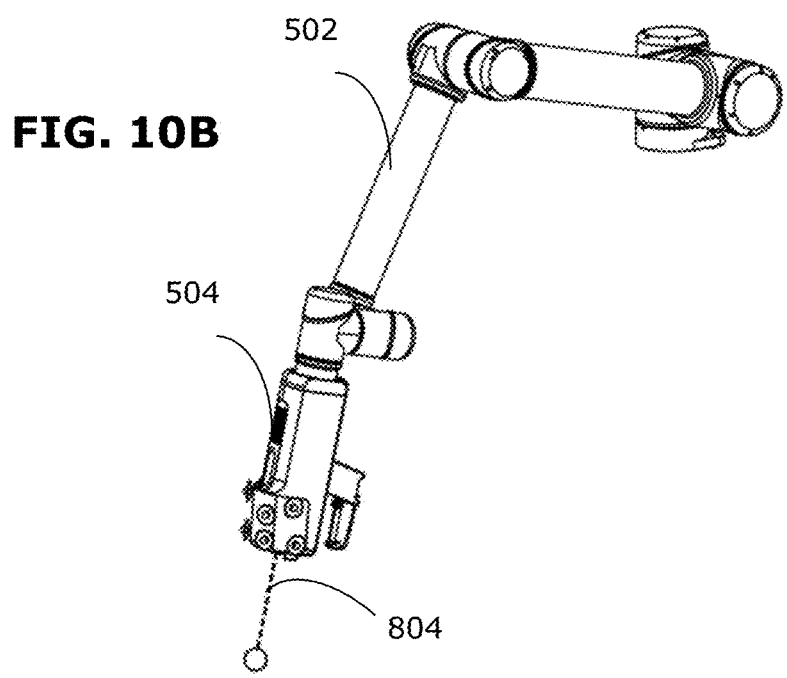

FIGS. 10A and 10B illustrate the movement of the end effector 504 when the positioning system 500 is controlled in stand-off mode from a first position of the end effector (FIG. 10A) to a second position of the end effector (FIG. 10B). In stand-off mode, the drive velocity is determined based on only external forces along a defined axis. External forces are projected to the defined axis and any perpendicular components are ignored or set to zero. Any external torques are ignored or set to zero. Alternatively, only external torques about the defined axis may be considered. For example, where the end effector 504 supports an imaging system, the defined axis may be the optical axis of the imaging system. Stand-off mode may then enable the end effector 504 to be moved along the optical axis, in order to change focus and/or zoom level of the captured image, without changing the center of focus. FIGS. 10A and 10B show the movement of the end effector 504 being constrained to a defined axis 804, in this case the optical axis of the imaging system supported by the end effector 504. As shown, the end effector 504 remains aligned with the defined axis 804 throughout its movements, and is moved closer and farther away from the focal point (represented by a circle). In some examples, the end effector 504 may rotate about the defined axis 804.

Figure 11A:
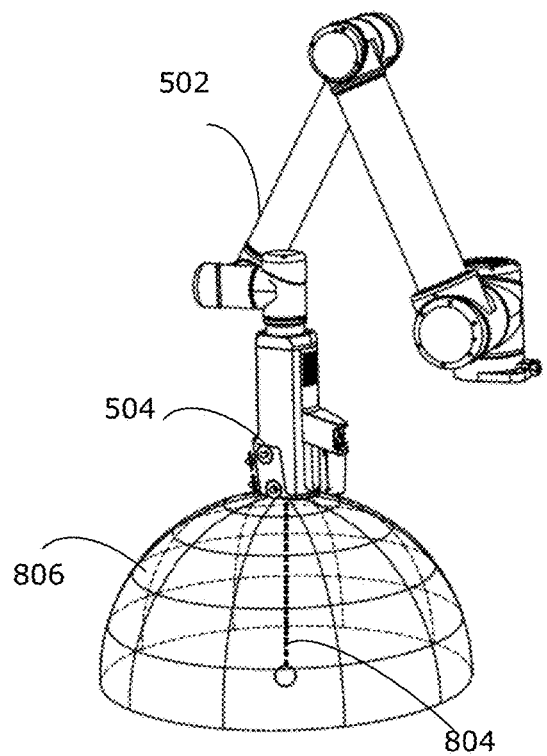
FIGS. 11A-11C illustrates the movement of the end effector when the positioning system is controlled in orbit mode from a first position of the end effector (FIG. 11A) to a second position of the end effector (FIG. 11B) and to a third position of the end effector (FIG. 11C).
Figure 11B:
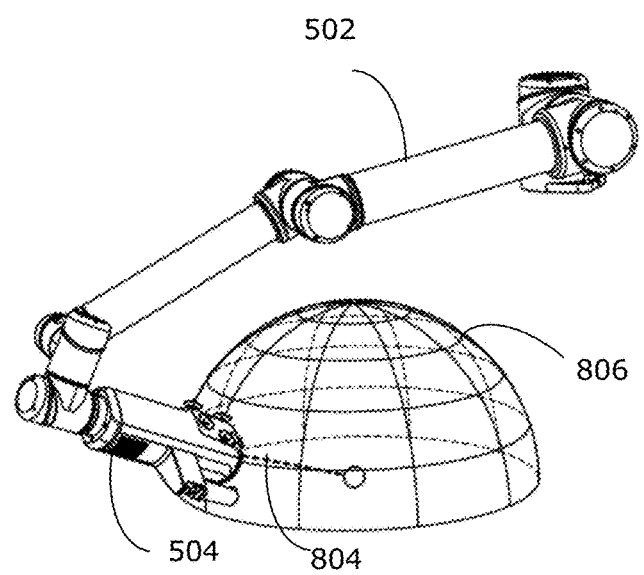
Figure 11C:
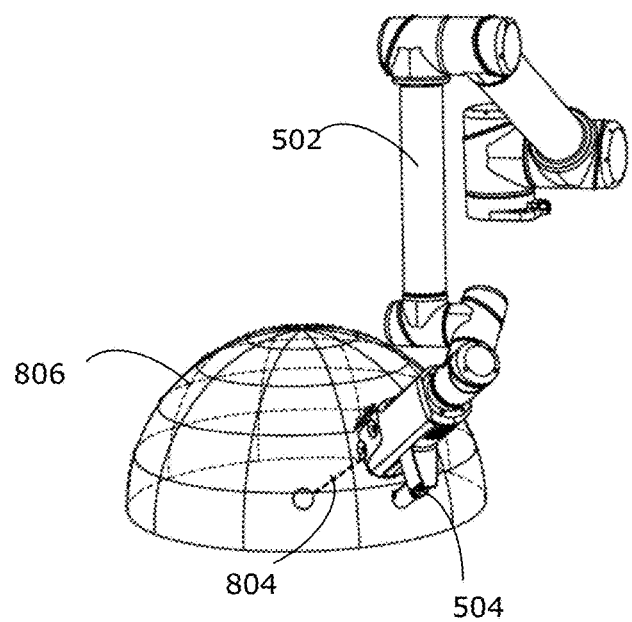

FIGS. 11A-11C illustrates the movement of the end effector 504 when the positioning system 500 is controlled in orbit mode from a first position of the end effector (FIG. 11A) to a second position of the end effector (FIG. 11B) and to a third position of the end effector (FIG. 11C). In orbit mode, the end effector 504 is constrained to move along the surface of a virtual sphere defined about a selected point of interest (POI). The POI may be selected preoperatively (e.g., during the planning of the procedure) or intraoperatively (e.g., using a tracked pointer tool or defined to be the focal point of the scope supported by the end effector 504). The location of the POI may be stored by the controller, and may be defined with reference to the end effector frame of reference. In some examples, the location of the POI may be defined with reference to a different frame of reference, for example a tracking frame of reference (e.g., using a tracking coordinate system defined by the tracking system 204) or a patient frame of reference, in which case a transformation to a common coordinate system (e.g., as described above with respect to FIG. 4) may be performed. The virtual sphere may be defined by a radius about the POI. The radius may be defined preoperatively or intraoperatively. For example, the radius may be defined by a safety distance that the end effector 504 should maintain to avoid contamination. In some examples, the radius may be defined by the focal distance of the scope supported by the end effector 504, so that the POI is maintained in focus.

To constrain movement of the end effector 504 along the surface of the virtual sphere, a plane is defined that is tangent to the virtual sphere and having a normal along the main axis of the end effector 504 (e.g., the optical axis of the scope supported by the end effector 504). Only external forces on the plane and external torques about the normal axis are used to determine the drive velocity. All other external forces and torques are ignored or set to zero. In some examples, all external torques are ignored or set to zero.

The drive velocity may then be determined in the tangent plane and then projected onto the virtual sphere (e.g., transforming velocity from the Cartesian coordinate system to a spherical coordinate system about the POI). FIGS. 11A-11C show the end effector 504 being moved along the surface of a virtual sphere 806 that is centered about a focal point (represented by a circle) of the imaging system supported by the end effector 504. As shown, the end effector 504 can translate along the surface of the virtual sphere 806 and can also rotate about the defined axis 804 (e.g., defined as the optical axis of the imaging system) from a first position (FIG. 11A) to a second position (FIG. 11B) and finally to a third position (FIG. 11C).

In some examples, orbit mode may constrain the end effector 504 to move along a virtual surface that is a shape other than a sphere. For example, orbit mode may constrain the end effector 504 to move along a virtual ovoid or virtual bubble encasing an area of interest, which may be defined in a manner similar to definition of the POI as described above.

Figure 12A:
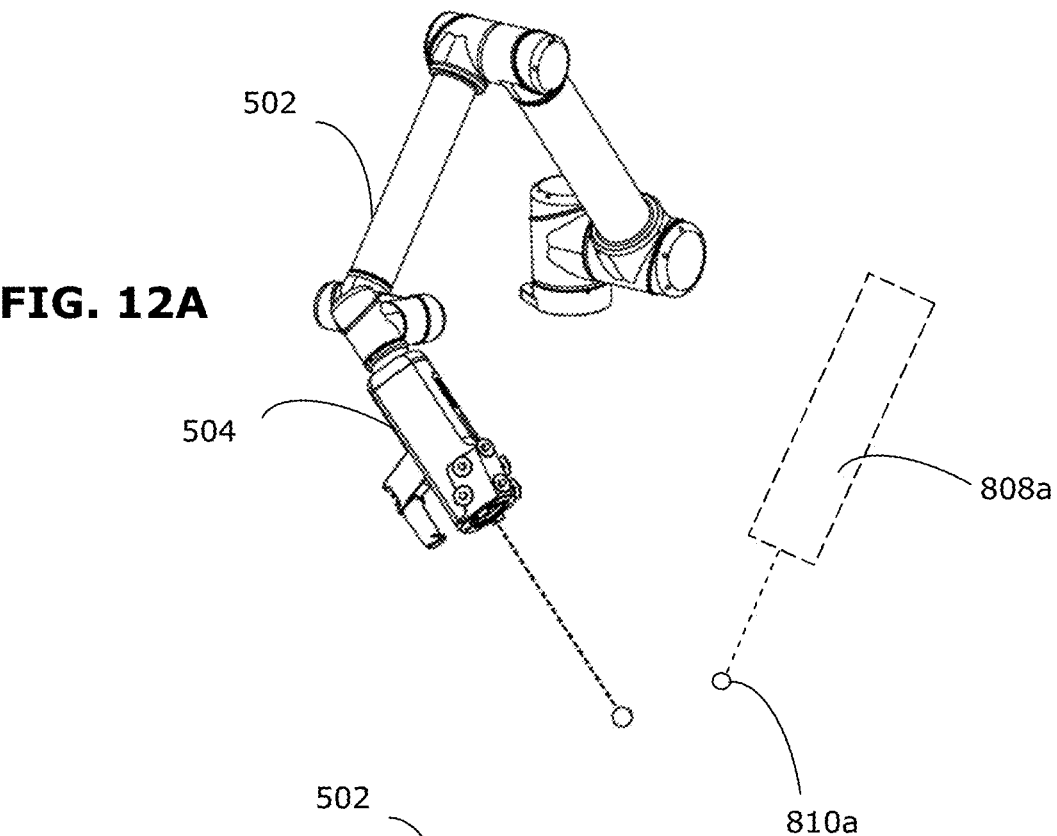
FIGS. 12A and 12B illustrates the movement of the end effector when the positioning system is controlled in memory mode from a first position of the end effector (FIG. 12A) to a second position of the end effector (FIG. 12B).
Figure 12B:
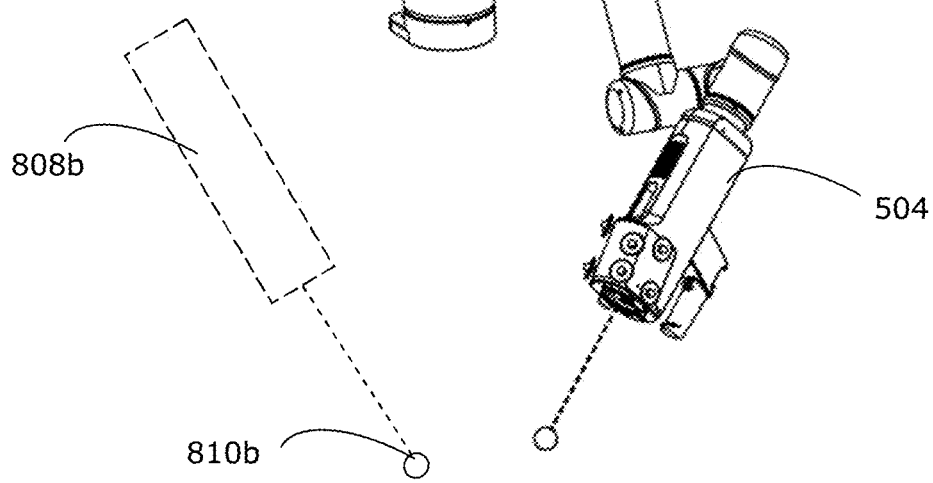

FIGS. 12A and 12B illustrates the movement of the end effector 504 when the positioning system 500 is controlled in memory mode from a first position of the end effector (FIG. 12A) to a second position of the end effector (FIG. 12B). In memory mode, the positioning system 500 controls the end effector 504 to move to one or more previously saved positions and orientations. A certain position and orientation of the end effector 504 may be stored by the positioning system 500 preoperatively (e.g., as part of planning for the procedure, or as a default) or intraoperatively (e.g., a user can save a current position and orientation of the end effector 504). When the external force(s)/torque(s) is detected, the end effector 504 is moved to the nearest saved position and orientation that is in the direction of the external force(s)/torque(s). Memory mode may enable a surgeon to restore the position and orientation of the end effector 504 to a desired previously saved position and orientation without having to explicitly select the saved position and orientation, and may be more intuitive to the surgeon. FIGS. 12A and 12B show the end effector 504 being moved between a first saved position/orientation 808a with a first focal point 810a and a second saved position/orientation 808b with a second focal point 810b. It should be noted that the end effector 504 can be moved to a saved position/orientation from any position/orientation, including from another saved position/orientation.

When the positioning system 500 is controlled in free mode, the drive velocity is determined based on all external forces and torques, without constraints. When no control mode has been selected, free mode may be used by default.

At 708, one or more joint movements of the positioning arm are calculated, in order to move the end effector 504 according to the drive velocity determined at 706. The calculation of joint movements may be performed using any suitable approach, for example using arm inverse kinematics. Any damping (e.g., to achieve smoother motion) or other physical constraints (e.g., avoiding self-collision) may be taken into account when calculating joint movements. It should be noted that the calculated joint movement(s) is(are) not limited to any one joint. Rather, the entire positioning arm 502, including all of the segments 508 and all of the joints 510, may be moved according to the drive velocity.

At 710, the controller communicates with the positioning arm 502 to cause the positioning arm 502 to move according to the calculated joint movement(s).

Information from the tracking system 204 of the navigation system 200 may also be taken into account when moving the positioning arm 502. For example, the controller may receive tracking information representing the tracked position and orientation of the positioning arm 502 and/or end effector 504 (e.g., where the positioning arm 502 or end effector 504 has tracking markers 518. The positioning arm 502 may be moved with respect to a tracking frame of reference. This may be used as part of or in parallel to the method 700.

Figure 13:
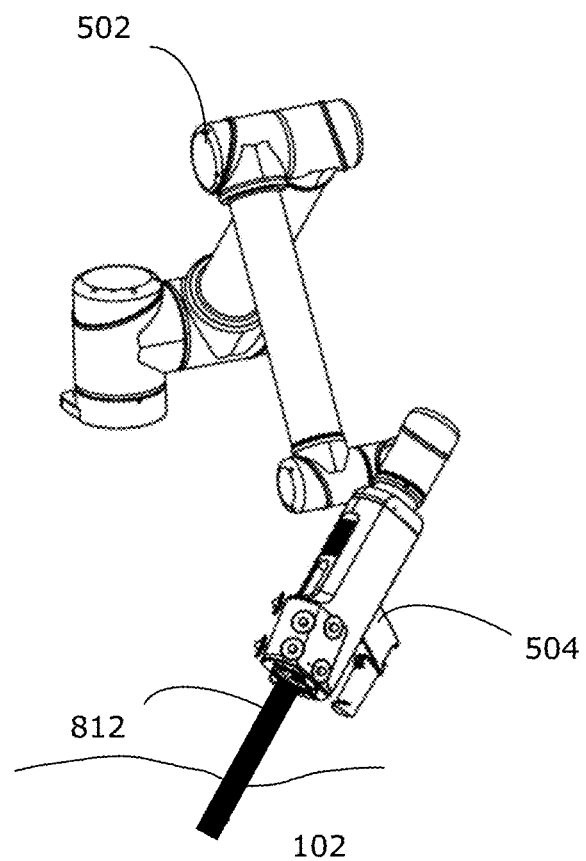
FIG. 13 illustrates a control mode for controlling movement of the positioning arm where sensing external forces and/or torques is used as a safety feature.

In some examples, a safety feature may also be implemented. This is illustrated in the example of FIG. 13, where a tool, such as an endoscope 812, is fitted to the end of the end effector 504. The endoscope 812 enters the body cavity of the patient 102. The endoscope 812, because it is coupled to the positioning arm 502, can be positioned using the positioning arm 502 in any suitable control mode and using any suitable control input. For example, the positioning arm 502 may be controlled using any non-manual input (that is, without manually moving the positioning arm 502 or applying external forces/torques to the positioning arm 502 directly), for example using a touch screen or other input device of the control and processing unit 300 controlling the positioning system 500. As a safety feature, the FMS 506 may detect forces applied to the surrounding tissues where the endoscope 812 enters into the body cavity. When the forces measured by the FMS 506 reaches a certain predefined safety threshold (e.g., tissue shear or tear forces), the positioning system 500 may be controlled to stop movement of the positioning arm 502 (and hence stop movement of the endoscope 812), to protect the tissue from incurring damage. Such a safety feature may be implemented for any tool that may pose a risk of damage to delicate tissues, for example any tool that will enter a body cavity of the patient 102.

The positioning system 500 may also be manually actuated without any assistance from the controller. That is, the positioning system 500 may be moved purely manually, similar to manual positioning of conventional robotic arms.

The computing device 300 may further have additional features that are configurable when operating the method 700, such as getting the positioning arm 700 to an initial ready position, using a tracked pointer to define a "no go" area in space where the positioning arm 700 is not permitted to breach, or a collision avoidance safety feature (e.g., using proximity sensors).

The assisted manual actuation described herein may also be useful for detecting and reacting to strain, collision or blockage of the end effector 504. For example, any obstruction of the end effector 504 may cause an external force or torque applied to the end effector 504, which is sensed by the FMS 506. Appropriate movement of the end effector 504 away from the obstruction may then be calculated and carried out according to the approach described above.

The positioning system 500 may provide additional features, such as tactile, visual and/or audio feedback, or the ability to adjust the sensitivity level of the FMS 506.

Although the positioning system 500 has been described in various examples as being used with or being part of a navigation system, the positioning system 500 may also be used without a navigation system. For example, instead of relying on tracking information to determine a location of a POI, the POI may be defined in other ways, such as by user input or by calculating the location of a focal point or focal plane of a scope held by the end effector 504. Thus, the positioning system 500 may be used in non-image guided procedures as well as in image-guided procedures.

Although the above discussion refers to the surgeon as being the user who controls and uses the examples of the present disclosure, it should be understood that the present disclosure is not limited to any specific user. In some examples, there may be a plurality of users involved.

Unlike conventional robotic arms, the disclosed methods and systems, in various examples, use a six-axis force/torque sensor approach rather than a joint torque sensor approach. A joint torque sensor approach uses torque sensors in each joint of a multi-joint robotic arm, and use the torques sensed at each joint to calculate forces at the end effector. Such an approach tends to complicate joint design and calculations. Further, it is typically difficult to distinguish whether an external force is being applied at an end effector or at a particular joint. In the disclosed methods and systems, forces/torques applied at the end effector are more directly detected using a FMS located at or close to the end effector, without having to consider the kinematics of each individual joint of the positioning arm. This results in a solution that may have better accuracy, reliability and be less computationally expensive.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level programming language. Accordingly, the program code may be written in C, C++, J++, or any other suitable programming language and may comprise modules or classes, as is known to those skilled in programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. An automated positioning system, the system comprising:
   a multi joint positioning arm having a distal end, the multi joint positioning arm comprising a plurality of segments and a plurality of joints, each joint of the plurality of joints independently movable;
   a plurality of end effectors configured to couple with a plurality of imaging systems, the plurality of end effectors disposed in relation to the multi joint positioning arm such that each end effector avoids interference with another end effector, each end effector of the plurality of end effectors respectively coupled with each imaging system of the plurality of imaging systems to enable switching among a plurality of imaging modes, each end effector of the plurality of end effectors comprising a handle, each end effector coupled with the distal end of the positioning arm, and each end effector of the plurality of end effectors providing at least one of a range of control corresponding to each imaging system of the plurality of imaging system;
   a plurality of force-moment sensors (FMSs) coupled with the plurality of end effectors, each FMS respectively coupled with each end effector, and each FMS configured to sense a force signal and a torque signal in relation to each end effector; and
   a controller in communication with the positioning arm and the plurality of FMSs, the controller configured to:
   determine, using signals from each FMS of the plurality of FMSs, at least one of an external force and an external torque applied to each end effector of the plurality of end effectors;
   determine a drive velocity for moving each end effector of the plurality of end effectors, based on at least one of the external force and the external torque, according to a selected available control mode of a plurality of available control modes;
   calculate at least one joint movement of the positioning arm for moving each end effector of the plurality of end effectors according to the drive velocity, whereby at least one calculated joint movement is provided; and
   cause the positioning arm to move according to the at least one calculated joint movement, wherein each joint of the plurality of joints is independently moved to effect an overall movement of the positioning arm,
   wherein, when the positioning system is in an orbit mode, movement of each end effector from a position to a subsequent position is constrained along a surface of a virtual sphere defined about a point of interest,
   wherein the point of interest is one of preoperatively selected and intraoperatively selected,
   wherein the virtual sphere is defined by a radius about the point of interest,
   wherein the radius is one of preoperatively defined and intraoperatively defined in relation to a focal distance of each imaging system coupled with each the end effector, and
   wherein the point of interest is maintained in focus by each imaging system.

2. The positioning system of claim 1,
   wherein the controller is further configured to determine the drive velocity by applying a transformation to at least one of the external force and the external torque, and
   wherein the controller is further configured to transform at least one of the external force and the external torque from an FMS frame of reference to an end effector frame of reference.

3. The positioning system of claim 1, wherein the controller is further configured to determine at least one of the external force and the external torque by respectively subtracting an internal force and an internal torque from a force and a torque detected by each FMS of the plurality of FMSs.

4. The positioning system of claim 1, wherein the plurality of available control modes comprises at least one of:
   a translation mode, wherein the drive velocity is determined based on only the external force;
   a roll mode, wherein the drive velocity is determined based on only the external torque;
   a stand-off mode, wherein the drive velocity is determined based on only the external force along a defined axis;
   an orbit mode, wherein the drive velocity is determined based on only the external force on a plane tangent to a defined surface and the external torque about a defined axis;
   a memory mode, wherein the drive velocity is determined to move each end effector to a saved position and a saved orientation; and
   a free mode, wherein the drive velocity is determined based on all external forces and all external torques.

5. The positioning system of claim 1,
   wherein the controller is further configured to implement a safety feature, and
   wherein the controller is further configured to:
   determine whether at least one of a force and a torque incident at each end effector at least one of meets and exceeds a predefined threshold;
   determine whether the drive velocity should be zero, based on whether at least one the force and the torque incident at each end effector at least one of meets and exceeds the predefined threshold; and
   cause the positioning arm to stop all joint movements.

6. The positioning system of claim 1, wherein each FMS is coupled with the handle of each end effector.

7. The positioning system of claim 6, wherein each FMS is coupled with each end effector at a location between the distal end of the positioning arm and the handle of each end effector.

8. The positioning system of claim 1, wherein each FMS is coupled with each end effector between the distal end of the positioning arm and each end effector.

9. The positioning system of claim 1, further comprising a plurality of tracking markers coupled with one of the positioning arm and each end effector, wherein the controller is further configured to:
receive tracking information from a navigation system, the tracking information representing a tracked position and a tracked orientation of at least one of the positioning arm and each end effector; and
cause the positioning arm to move relative to a tracking frame of reference.

10. The positioning system of claim 1, wherein each end effector is configured to support at least one of an imaging system and a medical instrument.

11. The positioning system of claim 1, further comprising a plurality of manual activation mechanisms, wherein the controller is further configured to cause the positioning arm to move in response to at least one of the external force and the external torque when each activation mechanism is activated.

12. The positioning system of claim 11, wherein each activation mechanism is respectively coupled with each end effector.

13. A method of controlling a multi joint positioning arm by way of an automated positioning system, the method comprising:
providing the automated positioning system, providing the automated positioning system comprising:
providing a multi joint positioning arm having a distal end, the multi joint positioning arm comprising a plurality segment and a plurality of joints, each joint of the plurality of joints independently movable;
providing a plurality of end effectors configured to couple with a plurality of imaging systems, the plurality of end effectors disposed in relation to the multi-joint positioning arm such that each end effector avoids interference with another end effector, each end effector of the plurality of end effectors respectively coupled with each imaging system of the plurality of imaging systems to enable switching among a plurality of imaging modes, each end effector of the plurality of end effectors comprising a handle, each end effector coupled with the distal end of the positioning arm, and each end effector of the plurality of end effectors providing at least one of a range of control corresponding to each imaging system of the plurality of imaging system;
providing a plurality of force-moment sensors (FMSs) coupled with the plurality of end effectors, each FMS respectively coupled with each end effector, and each FMS configured to sense a force signal and a torque signal in relation to each end effector; and
providing a controller in communication with the positioning arm and the plurality of FMSs, the controller configured to:
determine, using signals from each FMS of the plurality of FMSs, at least one of an external force and an external torque applied to each end effector of the plurality of end effectors;
determine a drive velocity for moving each end effector of the plurality of end effectors, based on at least one of the external force and the external torque, according to a selected available control mode of a plurality of available control modes;
calculate at least one joint movement of the positioning arm for moving each end effector of the plurality of end effectors according to the drive velocity, whereby at least one calculated joint movement is provided; and
cause the positioning arm to move according to the at least one calculated joint movement, wherein each joint of the plurality of joints is independently moved to effect an overall movement of the positioning arm;
by way of the controller,
determining, using signals from each FMS of the plurality of FMSs, the plurality of FMSs coupled with the positioning arm, at least one of an external force and an external torque applied to each end effector of the plurality of end effectors coupled with the distal end of the positioning arm;
determining a drive velocity for moving each end effector of the plurality of end effectors, based on at least one of the external force and the external torque, according to a selected available control mode of a plurality of available control modes;
calculating at least one joint movement of the positioning arm for moving each end effector of the plurality of end effectors according to the drive velocity, thereby providing at least one calculated joint movement; and
causing the positioning arm to move according to the at least one calculated joint movement, wherein each joint of the plurality of joints is independently moved to effect an overall movement of the positioning arm,
wherein, when the positioning system is in an orbit mode, controlling movement of each end effector from a position to a subsequent position by constraining movement along a surface of a virtual sphere defined about a point of interest,
wherein the point of interest is one of preoperatively selected and intraoperatively selected,
wherein the virtual sphere is defined by a radius about the point of interest.
wherein the radius is one of preoperatively defined and intraoperatively defined in relation to a focal distance of each imaging system coupled with each the end effector, and
wherein the point of interest is maintained in focus by each imaging system.

14. The method of claim 13,
wherein determining the drive velocity comprises applying a transformation to at least one of the external force and the external torque, and
wherein applying the transformation comprises transforming at least one of the external force and the external torque from an FMS frame of reference to each end effector frame of reference.

15. The method of claim 13, wherein determining at least one of the external force and the external torque comprises respectively subtracting an internal force and an internal torque from a force and a torque detected by each FMS of the plurality of FMSs.

16. The method of claim 13,
wherein determining the drive velocity comprises determining the drive velocity for moving each end effector, based on at least one of the external force and the external torque, according to the selected available control mode of the plurality of available control modes-comprising at least one of:

a translation mode, wherein the drive velocity is determined based on only the external force;
a roll mode, wherein the drive velocity is determined based on only the external torque;
a stand-off mode, wherein the drive velocity is determined based on only the external force along a defined axis;
an orbit mode, wherein the drive velocity is determined based on only the external force on a plane tangent to a defined surface and the external torque about a defined axis;
a memory mode, wherein the drive velocity is determined to move each end effector to a saved position and a saved orientation; and
a free mode, wherein the drive velocity is determined based on all external forces and all external torques.

17. The method of claim 13, further comprising implementing a safety feature by:
determining whether at least one of a force and a torque incident at the end effector at least one of meets and exceeds a predefined threshold;
determining whether the drive velocity should be zero, based on whether at least one the force and the torque incident at each end effector at least one of meets and exceeds the predefined threshold; and
causing the positioning arm to stop all joint movements.

18. The method of claim 13, further comprising:
receiving tracking information representing a tracked position and a tracked orientation of at least one of the positioning arm and each end effector; and
causing the positioning arm to move relative to a tracking frame of reference.

19. The method of claim 13, further comprising causing the positioning arm to move in response to at least one of the external force and the external torque when a manual activation mechanism is activated.

20. A medical navigation system comprising:
a positioning system, the positioning system comprising:
a multi joint positioning arm having a distal end, the multi joint positioning arm comprising a plurality of segments and a plurality of joints, each joint of the plurality of joints independently movable;
a plurality of end effectors configured to couple with a plurality of imaging systems, the plurality of end effectors disposed in relation to the multi joint positioning arm such that each end effector avoids interference with another end effector, each end effector of the plurality of end effectors respectively coupled with each imaging system of the plurality of imaging systems to enable switching among a plurality of imaging modes, each end effector of the plurality of end effectors comprising a handle, each end effector coupled with the distal end of the positioning arm, and each end effector of the plurality of end effectors providing at least one of a range of control corresponding to each imaging system of the plurality of imaging system;
a plurality of force-moment sensors (FMSs) coupled with the plurality of end effectors, each FMS respectively coupled with each end effector, and each FMS configured to sense a force signal and a torque signal in relation to each end effector; and
a controller in communication with the positioning arm and the plurality of FMSs, the controller configured to:
determine, using signals from each FMS of the plurality of FMSs, at least one of an external force and an external torque applied to each end effector of the plurality of end effectors;
determine a drive velocity for moving each end effector of the plurality of end effectors, based on at least one of the external force and the external torque, according to a selected available control mode of a plurality of available control modes;
calculate at least one joint movement of the positioning arm for moving each end effector of the plurality of end effectors according to the drive velocity, whereby at least one calculated joint movement is provided; and
cause the positioning arm to move according to the at least one calculated joint movement, wherein each joint of the plurality of joints is independently moved to effect an overall movement of the positioning arm;
at least one of: an imaging system and a medical instrument supported by each end effector of the plurality of end effectors;
a plurality of tracking markers coupled with at least one of the positioning arm, each end effector of the plurality of end effectors of the positioning system, the camera, the scope, and the medical instrument; and
a tracking system for tracking the plurality of tracking markers,
wherein the controller of the positioning system is further configured to:
receive tracking information from the navigation system; and
cause the positioning arm to move relative to a tracking frame of reference,
wherein, when the positioning system is in an orbit mode, controlling movement of each end effector from a position to a subsequent position by constraining movement along a surface of a virtual sphere defined about a point of interest,
wherein the point of interest is one of preoperatively selected and intraoperatively selected,
wherein the virtual sphere is defined by a radius about the point of interest.
wherein the radius is one of preoperatively defined and intraoperatively defined in relation to a focal distance of each imaging system coupled with each the end effector, and wherein the point of interest is maintained in focus by each imaging system.

* * * * *